US00PP37749P2

(12) United States Plant Patent
Egger

(10) Patent No.: US PP37,749 P2
(45) Date of Patent: Oct. 6, 2026

(54) ***SEDUM* PLANT NAMED 'Mocha Magic'**

(50) Latin Name: *Sedum telephium*
Varietal Denomination: Mocha Magic

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 19/339,620

(22) Filed: Sep. 25, 2025

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
See application file for complete search history.

(56) References Cited

PUBLICATIONS https://www.floraldaily.com/article/9613134/terra-nova-nurseries-showcases-color-changing-sedum-and-heuchera-varieties/ Retrieved from the Internet Dec. 11, 2025.*
https://www.soonerplantfarm.com/plant/sedum-mocha-magic; Retrieved from the Internet Dec. 11, 2025.*
Trevarthan et al., "Terra Nova Nurseries unveils new catalog and varieties," *Nursery Management*, 3 pages, Jul. 16, 2024.
"Sunsparkler® Firecracker Sedum" Sooner Plant Farms, 6 pages, (www.soonerplantfarm.com/plant/sedum-sunsparkler-firecracker), retrieved on Apr. 10, 2026.

* cited by examiner

*Primary Examiner* — Susan McCormick Ewoldt
(74) *Attorney, Agent, or Firm* — Klarquist Sparkman, LLP

(57) ABSTRACT

A new and distinct *Sedum* cultivar named 'Mocha Magic' distinguished by its foliage color, which can change from yellow-green to violet-blue to greyed purple through maturity and light exposure, its habit, which keeps in rainy weather, and its brown inflorescence.

4 Drawing Sheets

Latin name of the genus and species of the plant claimed: *Sedum telephium.*

Variety designation: 'Mocha Magic'.

BACKGROUND

The present application relates to a new and distinct cultivar of *Sedum* named 'Mocha Magic'. *Sedum* is in the family Crassulaceae. The new cultivar originated as a part of a planned breeding program to produced compact, multi-crowned *Sedums.*

SUMMARY

The new cultivar 'Mocha Magic' is distinguished from other *Sedum* varieties at least due to the following unique combination of characteristics:

1. Foliage changing from yellow-green to violet-blue to greyed purple through maturity and light exposure
2. Keeps habit in rainy weather
3. Brown inflorescence The parents of 'Mocha Magic' are undescribed and unpatented proprietary seedlings. The new variety is distinct from other known *Sedum* varieties, for example as compared to 'Peach Pearl' (unpatented), 'Mocha Magic' has a larger habit and its flowers are less pink. Compared to 'Dark Magic' (U.S. Plant Pat. No. 27,619), 'Mocha Magic' has a larger habit, and an overall coloring that is much more brown, including the inflorescence, and does not reach as dark of pigmentation when exposed to full sun. Compared to 'Class Act' (U.S. Plant Pat. No. 20,125) 'Mocha Magic' has a larger overall habit, its inflorescence is less pink, and its foliage is much less green.

The new cultivar has been reproduced by asexual propagation (tip cuttings and tissue culture using growing tips). Each of the progeny exhibits identical characteristics to the original plant. Asexual propagation by cuttings and tissue culture using standard micropropagation techniques with terminal and lateral shoots as done in Canby, Oregon, shows that the characteristics described herein come true to form, are firmly fixed, and are established and transmitted through succeeding propagations.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Color descriptions and other terminology are used in accordance with their ordinary dictionary descriptions, unless the context clearly indicates otherwise. Color descriptions used herein are made with reference to *The Royal Horticultural Society Colour Chart,* $5^{th}$ edition, 2007.

Figure 1:
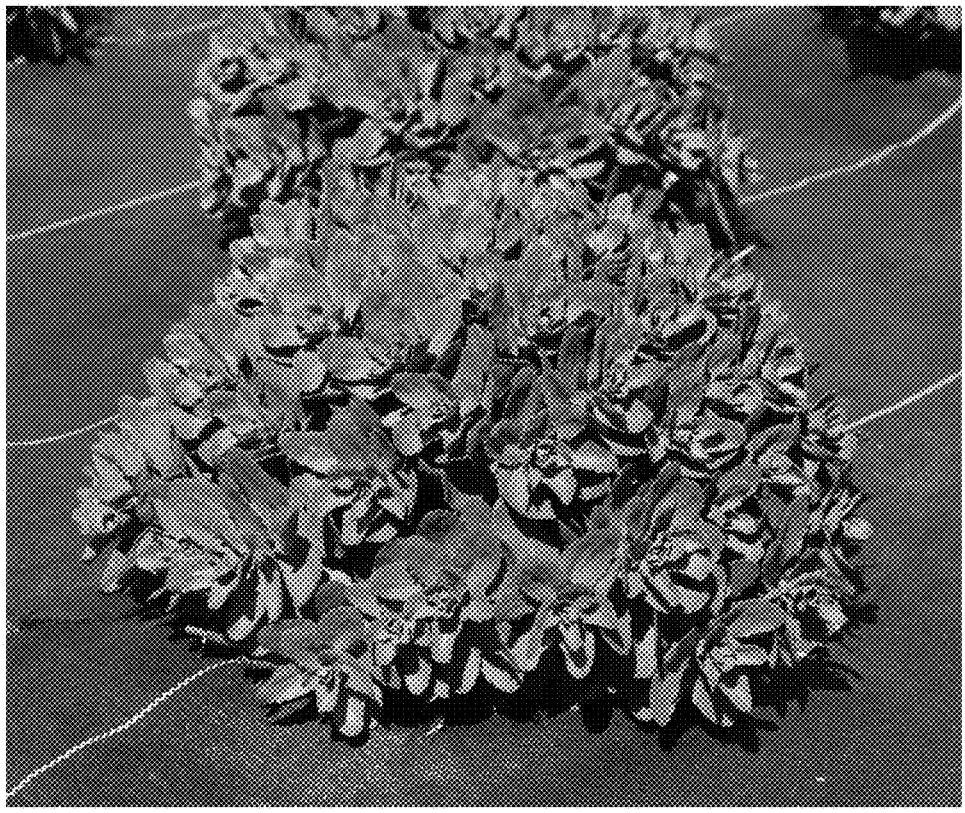
FIG. 1 shows a 15-month-old plant field grown in full sun in Canby, OR, photographed in Early April.
Figure 2:
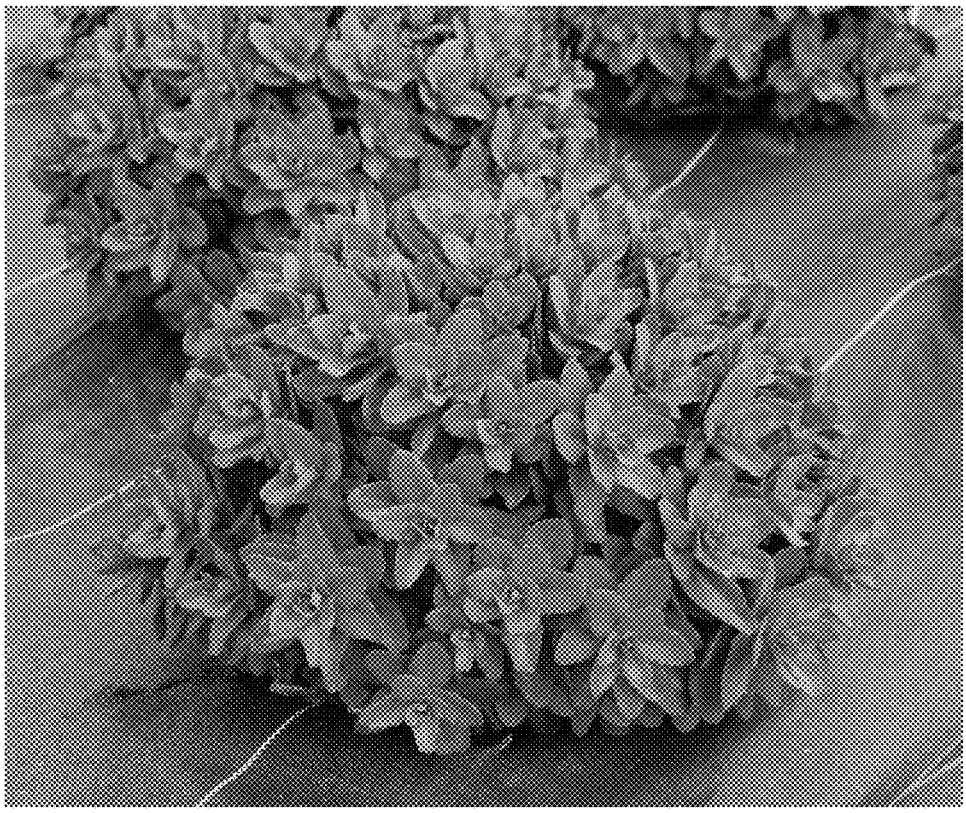
FIG. 2 shows the same 15-month-old plant field grown in full sun in Canby, OR, photographed in late April of the same year.
Figure 3:
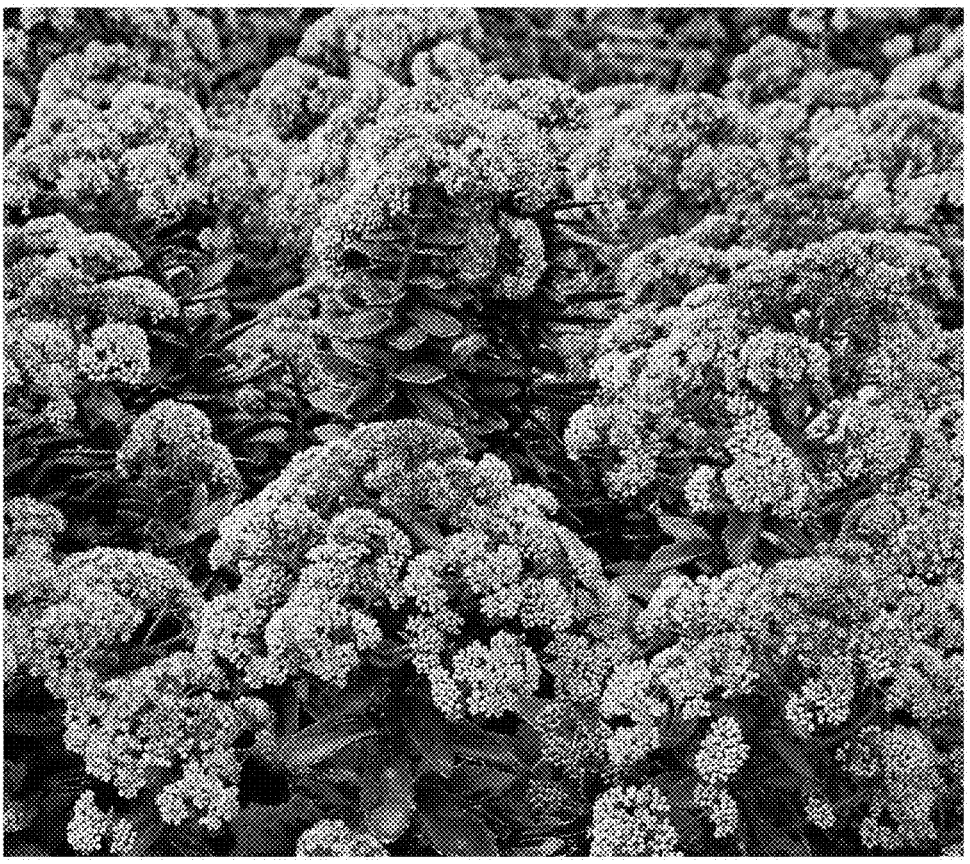
FIG. 3 shows a close-up of blooming inflorescences on a 6-year-old plant field grown in full sun in Canby, OR, photographed in late August.
Figure 4:
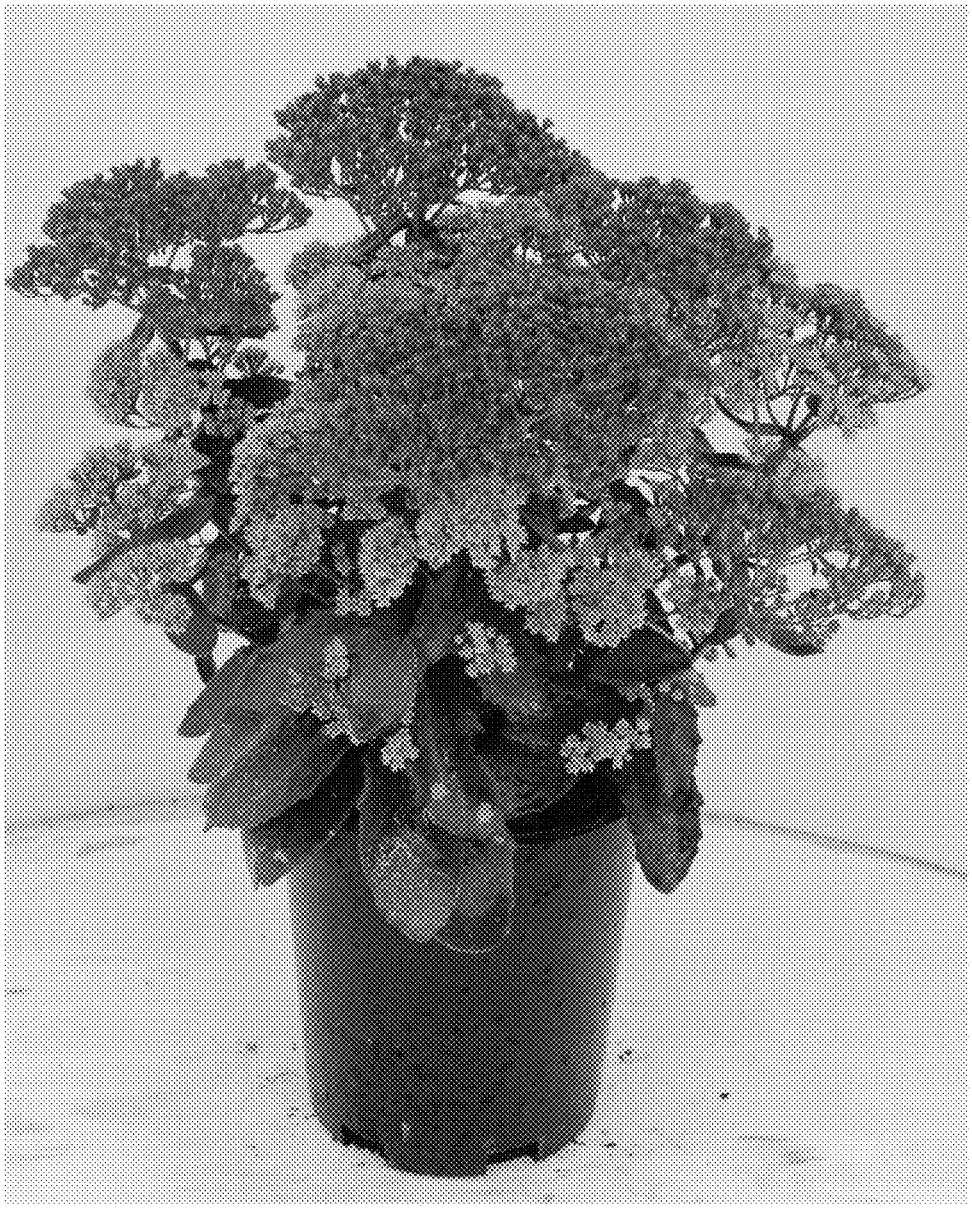
FIG. 4 shows a 6-month-old plant greenhouse grown in Canby, OR, photographed in September.

The color photographs show typical specimens of the new cultivar and depict the color as nearly true as is reasonably possible. It should be noted that colors may vary, for example due to lighting conditions at the time the photograph is taken. Therefore, color characteristics of this new cultivar should be determined with reference to the observations described herein, rather than from the photograph alone.

DETAILED PLANT DESCRIPTION

The following is a detailed description of the new *Sedum* cultivar based on observations taken in the month of September of a 9-month-old asexually reproduced progeny that was container grown in an unheated hoophouse in Hillsboro, Oregon. Hillsboro is Zone 8b on the USDA Hardiness map. For 2024 temperatures ranged from an average high of 87.1° F. in July to an average low of 34.3° F. in January. Annual rainfall in 2024 for Hillsboro was 41.1 inches. A 6-year-old field grown specimen grown in full sun in Canby, OR, was also used. Canby is Zone 8 on the USDA Hardiness map. Temperatures range from a high of 95° F. in August to an average of 32° F. in January. Normal rainfall in Canby is 42.8 inches per year.

Plant:

*Type*.—Herbaceous perennial.

*Hardiness*.—USDA zones 4-9.

*Size*.—Up to 81 cm tall at top of inflorescence and 76 cm at widest point when mature.

*Habit*.—Upright.

*Vigor*.—Excellent.

Stem:

*Type*.—Branching.

*Number*.—3-10.

*Size*.—38 cm tall, 1.5 cm wide at base.

*Internode length*.—1.5 cm to 3.0 cm.

*Surface texture*.—Glabrous, glossy.

*Color*.—Red-purple RHS 59A in light/sun exposed areas, closest to yellow-green RHS 147C in shaded areas.

Leaf:

*Type*.—Simple.

*Arrangement*.—Alternate.

*Shape*.—Ovate.

*Apex*.—Acute to rounded.

*Base*.—Truncate to slightly cordate.

*Venation*.—Pinnate.

*Margins*.—Irregularly serrate.

*Blade size*.—Up to 7 cm wide and 10 cm long.

*Surface*.—Glabrous on both sides.

*Texture*.—Succulent.

*Petiole*.—None leaves sessile.

*Leaf color*.—Topside: Immature leaves are closest to yellow-green RHS 147A in shade, in full sun closest to greyed-green N189B; mature leaves are closest to violet-blue RHS N92A in shade to greyed purple N187A with greyed-purple group 185A in sun. Bottom: Varies between RHS N138B and closest to yellow-green RHS 147B, in full sun closest to greyed-green RHS N189A. Top Venation: Closest to yellow-green RHS 147A with midrib speckled with RHS 187B, in full sun closest to purple RHS N77C. Bottom Venation: Varies from yellow-green RHS 145A to green RHS 138B sometimes with speckles of red-purple RHS 60B, in full sun closest to between greyed-purple RHS N187A and B.

Inflorescence:

*Type*.—Terminal, corymbose, umbel-like.

*Number of flowers*.—Approximately 950 to over 1000 per branched stem.

*Size*.—Up to 21 cm wide and 15 cm tall.

*Peduncle*.—None.

*Rachis*.—Color: Yellow-green RHS 147C to red-purple RHS 59A, in full sun also red purple RHS 59A. Length and Width: Up to 15 cm long and 1 cm wide. Texture: Succulent, glabrous.

*Pedicels*.—Color: Closest to yellow-green RHS 147B, in full sun red-purple RHS 59A to greyed-green RHS 197A. Length and Width: Up to 1 mm wide and 5-7 mm long. Texture: Succulent, glabrous.

*Bloom period*.—August through September in Canby, Oregon.

Flower bud:

*Size*.—Up to 2 mm wide and 3 mm tall.

*Description*.—Conical and stellate.

*Color*.—Green-white RHS 157C at base brushed with greyed-orange RHS 177D and greyed-red RHS 180D at the tip, in full sun closest to white RHS N155D brushed with greyed-red RHS 182B and closest to purple RHS 75D.

Flower:

*Type*.—Complete, actinomorphic.

*Shape*.—Stellate.

*Size*.—Up to 7 mm wide and 5 mm tall.

*Corolla description*.—Size: 7 mm wide 6 mm deep. Number of Petals: 5. Petal Shape: Lanceolate. Petal Size: 4 mm long and 2 mm wide. Petal Margins: Entire. Tip: Acuminate. Base: Rounded. Petal Texture/Surface: Both sides glabrous. Petal Color: The inside is white RHS 155A tipped with greyed-red RHS 179D, the outside is white RHS NN155B with greyed-yellow RHS 162C and greyed- orange N170D at the tip. Petals dry to greyed-orange RHS 173D. In full sun, the outside is closest to orange-white RHS 159B, the inside is closest to greyed-orange RHS 177D, and dries to greyed-red RHS 182A.

*Calyx description*.—Size: 1 mm tall and 3 mm wide. Shape: Stellate. Lobes: 5. Division: Divided to the base. Margins: Entire. Tip: Acuminate. Surface/Texture: Glabrous. Color: Closest to green RHS N138C, in full sun closest to greyed-red RHS 182C.

*Stamen description*.—Number: 10, 5 alternately fused at base to petals. Length: 4 mm. Filament Length: 3.75 mm. Anther Length: 0.25 mm. Filament Color: Semi-translucent, closest to white RHS NN155A, in full sun closest to white RHS N155B. Anther Color: Closest to greyed-purple RHS 183C, dries to greyed-orange RHS 177A. In full sun, closest to greyed-orange RHS 176B, and dries closest to greyed-orange RHS 176A. Pollen Color: Yellow RHS 10D. Pollen Quantity: Moderate to significant.

*Pistil description*.—Number of Carpels: 5. Size of Carpels: 4.5 mm long and 2.5 mm wide. Carpel Color: Starting entirely yellow-green RHS 145C, the top 4 mm matures to greyed-red RHS 178A. In full sun, it starts as greyed-yellow RHS 162D and matures to red RHS 47A.

*Description of nectary at base of each carpel* (5 *in total*).—Yellow-orange RHS 17C; measuring 2 mm, curved.

*Fragrance*.—Mild, sweet.

*Lastingness*.—Each stem lasts up to a month.

I claim:

1. A new and distinct *Sedum* plant named 'Mocha Magic' substantially as illustrated and described herein.

* * * * *